US010258724B2

(12) United States Patent
Demou et al.

(10) Patent No.: US 10,258,724 B2
(45) Date of Patent: Apr. 16, 2019

(54) VAD WITH AORTIC VALVE OPENING DETECTION

(71) Applicant: HeartWare, Inc., Miami Lakes, FL (US)

(72) Inventors: Zoe Demou, Miami, FL (US); Carlos Reyes, Davie, FL (US); Pedro Grave De Peralta, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 13 days.

(21) Appl. No.: 15/664,878

(22) Filed: Jul. 31, 2017

(65) Prior Publication Data

US 2018/0028735 A1 Feb. 1, 2018

Related U.S. Application Data

(60) Provisional application No. 62/369,528, filed on Aug. 1, 2016.

(51) Int. Cl.
*A61M 1/10* (2006.01)
*A61M 1/12* (2006.01)

(52) U.S. Cl.
CPC ........ *A61M 1/1086* (2013.01); *A61M 1/1036* (2014.02); *A61M 1/122* (2014.02);
(Continued)

(58) Field of Classification Search
CPC ........ A61M 1/10; A61M 1/12; A61M 1/1086; A61M 1/1087; A61M 2205/3331; A61M 2230/04; A61M 2230/30; A61M 1/122; A61M 1/1031; A61M 2230/005; A61M 1/101; A61M 2205/3334; A61M 1/1005; A61M 1/1015; A61M 2205/52; G06N 3/08
(Continued)

(56) References Cited

U.S. PATENT DOCUMENTS 8,897,873 B2    11/2014   Schima et al.
2012/0245681 A1  9/2012   Casas et al.
(Continued)

FOREIGN PATENT DOCUMENTS

WO      0228280 A1    4/2002
WO    201504022 A2    3/2015
(Continued)

OTHER PUBLICATIONS

Marcus Granegger et al., Continuous monitoring of aortic valve opening in rotary blood pump patients, 10.1109/TBME.2015. 2489188, IEEE Transactions on Biomedical Engineering.
(Continued)

*Primary Examiner* — Carl H Layno
*Assistant Examiner* — Jon Eric C Morales
(74) *Attorney, Agent, or Firm* — Christopher & Weisberg, P.A.

(57) ABSTRACT

The present disclosure provides for methods and devices for determining the probability of a patient's aortic valve being open or closed. In one embodiment, a plurality of flow rate data points are obtained from a blood pump, a portion of the flow rate data points are identified, first and second index values characterizing properties of at least part of the identified portion of the flow rate data points determined using only arithmetic and/or exponentiation operations, and a probability is determined of whether the patient's aortic valve is open or closed based on the first and second index values.

15 Claims, 10 Drawing Sheets

(52) U.S. Cl.
CPC ............... *A61M 2205/3334* (2013.01); *A61M 2205/3365* (2013.01); *A61M 2205/50* (2013.01); *A61M 2230/04* (2013.01)

(58) Field of Classification Search
USPC .......................................................... 607/17
See application file for complete search history.

(56) References Cited

U.S. PATENT DOCUMENTS

| | | |
|---|---|---|
| 2015/0367048 A1 | 12/2015 | Brown et al. |
| 2016/0166211 A1 | 6/2016 | Brown et al. |
| 2016/0206797 A1* | 7/2016 | Karch ................. A61M 1/1086 |

FOREIGN PATENT DOCUMENTS

| | | |
|---|---|---|
| WO | 2015040221 A2 | 3/2015 |
| WO | 2016044889 A2 | 3/2016 |

OTHER PUBLICATIONS

Christopher Hayward et al., Pump Speed Waveform Analysis to Detect Aortic Valve Opening in Patients on Ventricular Assist Device Support, Artif Organs, vol. 39, No. 8, 2015.

International Search Report and Written Opinion dated Oct. 10, 2017, for corresponding International Application No. PCT/US2017/044698; International Filing Date: Jul. 31, 2017 consisting of 12-pages.

* cited by examiner

Aortic Valve State: LDA Results Summary

| Set # | description | # pred. | predictors | Accuracy | Sensitivity | Specificity | Balanced Accuracy |
|---|---|---|---|---|---|---|---|
| 1 | Single pulse | 6 | raw_Intg; tpoints; Dt; SdiffY; SsqrDiffY; normEr | 0.8145 | 0.7151 | 0.8949 | 0.8050 |
| 2 | Single pulse | 3 | raw_Intg; Dt; normEr | 0.8116 | 0.7075 | 0.8959 | 0.8017 |
| 3 | Single pulse | 3 | Dt; SsqrDiffY; normEr | 0.8063 | 0.6861 | 0.9037 | 0.7949 |
| 4 | Single pulse | 3 | raw_Intg; Dt; SsqrDiff | 0.7752 | 0.6890 | 0.8449 | 0.7669 |
| 5 | Single pulse | 2 | Dt; normEr | 0.8068 | 0.6851 | 0.9053 | 0.7952 |
| 6 | Single pulse | 2 | SsqrDiffY; normEr | 0.7454 | 0.5701 | 0.8873 | 0.7287 |
| 7 | Single pulse | 6 | raw_Intg; tpoints; Dt; SsqrDiffY; S(Y-Ym)^3; normEr | 0.8152 | 0.7166 | 0.8949 | 0.8058 |
| 8 | Single pulse | 2 | S(Y-Ym)^3; normEr | 0.7242 | 0.5219 | 0.8878 | 0.7049 |
| 9 | Single pulse | 3 | Dt; S(Y-Ym)^3; normEr | 0.8061 | 0.6844 | 0.9046 | 0.7945 |
| 10 | LDA | 3 | R(Dt), R(S(Y-Ym)^3, R(normER) | 0.8458 | 0.6754 | 0.9838 | 0.8296 |
| 11 | LDA | 3 | R(Dt), R(normErr), R(SsqrDiffY) | 0.8452 | 0.6747 | 0.9832 | 0.8290 |
| 12 | LDA | 2 | R(Dt), R(normErr) | 0.8449 | 0.6725 | 0.9845 | 0.8285 |
| 13 | LDA | 3 | R(Dt), R(S(Y-Ym)^3), R(SsqrDiffY) | 0.8298 | 0.6818 | 0.9496 | 0.8157 |
| 14 | LDA | 5 | R(raw_Intg), R(tpoints), R(Dt), R(S(Y-Ym)^3, R(normErr) | 0.8266 | 0.6850 | 0.9412 | 0.8131 |
| 15 | LDA | 6 | R(raw_Intg), R(tpoints), R(Dt), R(S(Y-Ym)^3, R(normErr), R(SsqrDiffY) | 0.8244 | 0.6883 | 0.9344 | 0.8114 |
| 16 | LDA + R(F) | 3 | R(Dt), R(normErr), R(SsqrDiffY), R(F) | 0.8532 | 0.7306 | 0.9527 | 0.8417 |
| 17 | 5 pulse-ave | 6 | 5ave_raw_Intg, 5ave_tpoints, 5ave_Dt, 5ave_SsqrDiffY, 5ave_S(Y-Ym)^3, 5ave-normEr | 0.8579 | 0.7631 | 0.9346 | 0.8488 |
| 18 | 5 pulse-ave | 3 | 5ave_Dt, 5ave_SsqrDiffY, 5ave_normEr | 0.8578 | 0.7725 | 0.9268 | 0.8496 |
| 19 | 5 pulse-ave | 3 | 5ave_Dt, 5ave_S(Y-Ym)^3, 5ave_normEr | 0.8591 | 0.7755 | 0.9268 | 0.8512 |
| 20 | 5 pulse-ave | 2 | 5ave_Dt, 5ave_normEr | 0.8592 | 0.7752 | 0.9272 | 0.8512 |
| 21 | 10 pulse-ave | 6 | 10ave_raw_Intg, 10ave_tpoints, 10ave_Dt, 10ave_SsqrDiffY, 10ave_S(Y-Ym)^3, 10ave_normEr | 0.8844 | 0.7900 | 0.9608 | 0.8754 |
| 22 | 10 pulse-ave | 2 | 10ave_Dt, 10ave_normEr | 0.8784 | 0.8010 | 0.9411 | 0.8710 |
| 23 | 10 pulse-ave | 2 | 10ave_S(Y-Ym)^3, 10ave_normEr | 0.7524 | 0.5670 | 0.9023 | 0.7347 |

VAD WITH AORTIC VALVE OPENING DETECTION

CROSS-REFERENCE TO RELATED APPLICATION

This application is related to and claims priority to U.S. Provisional Patent Application Ser. No. 62/369,528, filed Aug. 1, 2016, entitled VAD WITH AORTIC VALVE OPENING DETECTION, the entirety of which is incorporated herein by reference.

STATEMENT REGARDING FEDERALLY SPONSORED RESEARCH OR DEVELOPMENT n/a

TECHNICAL FIELD

The present invention relates to a method and system for detecting whether the aortic valve is open in a patient with an implantable blood pump.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD."

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source. The VAD typically includes a control system which controls operation of the power source so as to drive the impeller at a set rotational speed and thus provide constant pumping action.

VADs can be used to assist the heart of subjects suffering from conditions which impair the pumping ability of the heart. Such assistance can be provided permanently, or while the subject awaits a suitable heart transplant. In other cases, the assistance provided by the VAD allows the heart to heal.

The VAD pumping mechanism may be a radial flow pump, such as the HVAD® Pump manufactured by HeartWare Inc. in Miami Lakes, Fla., USA. The HVAD® Pump is further discussed in U.S. Pat. No. 8,512,013, the disclosure of which is hereby incorporated herein in its entirety. In operation, the blood pump draws blood from a source such as the right ventricle, left ventricle, right atrium, or left atrium of a patient's heart and propels the blood into an artery such as the patient's ascending aorta or peripheral artery. Due to the nature of the application, the pumping mechanism must be highly reliable. Patient comfort is also a significant consideration. In addition to the pumping mechanism, the device may include a controller and the drive electronics for the pumping mechanism. The controller and drive electronics may receive power from an external power source. That power may be used to drive a motor of the pumping mechanism at a desired speed.

SUMMARY

The present invention advantageously provides a method for determining whether a patient's aortic valve is open or closed comprises obtaining a plurality of flow rate data points from a blood pump implanted within the patient, each flow rate data point indicating a then current flow rate of blood exiting the pump. A portion of the flow rate data points associated with systole of a given cardiac cycle of the patient is identified. A first index value characterizing a first property of at least part of the identified portion of the flow rate data points is determined. A second index value characterizing a second property of at least part of the identified portion of the flow rate data points is determined. Whether the patient's aortic valve is one of open and closed based on the first and second index values is determined. A speed of an impeller of the blood pump is adjusted in response to the determining whether the patient's aortic valve open.

In another aspect of this embodiment, the method further includes determining a first derivative for each of the obtained plurality of flow rate data points, wherein at least one of the first and second index values is determined based on the determined first derivatives.

In another aspect of this embodiment, the first derivative for each given flow rate data point is determined by the difference between said flow rate data point and the preceding flow rate data point.

In another aspect of this embodiment, identifying a portion of the flow rate data points associated with systole comprises determining a running average of flow rate and comparing the obtained flow rate data points to the running average, wherein a flow rate data point crossing above a crossover value of the running average is indicative of a beginning of systole, and a flow rate data point crossing below a crossover value of running average is indicative of an end of systole, and identifying the portion of flow rate data points above the running average as associated with systole.

In another aspect of this embodiment, identifying a portion of the flow rate data points associated with systole comprises determining a first derivative of each of the flow rate data points and identifying the portion of flow rate data points for which the first derivative decreases as associated with systole.

In another aspect of this embodiment, the first index value characterizes skew of the identified portion of the flow rate data points, and wherein the second index value characterizes smoothness of the identified portion of the flow rate data points.

In another aspect of this embodiment, the first index value characterizing skew is determined based on the difference in time between the flow rate data point indicating maximum flow rate and the midpoint of the identified portion of the flow rate data points.

In another aspect of this embodiment, the second index value characterizing smoothness is determined based on a mean linear square error between the first derivatives of the flow rate data points and a best fit line.

In another aspect of this embodiment, the mean linear square error is determined based at least in part on (i) a total number of evaluated flow rate data points, (ii) a sum of the first derivatives of the evaluated flow rate data points, and (iii) a product of (i) and (ii).

In another aspect of this embodiment, further comprising determining whether the patient's aortic valve is one of open and closed is based on a running average of the first and second index values for five previous cardiac cycles.

In another aspect of this embodiment, further comprising determining whether the patient's aortic valve is one of open and closed is based on a scaled linear combination of the first and second index values.

In another aspect of this embodiment, the scaled linear combination is based on a plurality of coefficients previously determined during a linear discriminant analysis using the first and second indices.

In another embodiment, a method for controlling operation of a blood pump implanted in a patient comprises obtaining flow rate data from the pump, the flow rate data indicating a rate of flow of blood exiting the pump. Whether the patient's aortic valve is one of open and closed based on the obtained flow rate data is repeatedly determined. If it is determined that the patient's aortic valve is closed based on one or more determinations an operating speed of the pump is reduced.

In another aspect of this embodiment, for each determination whether the patient's aortic valve is one of open and closed, a corresponding certainty value indicating a degree of certainty of the determination is determined, wherein reducing an operating speed of the pump is based on one or more determinations and the corresponding certainty values.

In another aspect of this embodiment, if it is determined that the patient's aortic valve is closed, the operating speed of the pump is reduced to a preset base speed.

In another aspect of this embodiment, if it is determined that the patient's aortic valve is closed, the operating speed of the pump is reduced until it is determined that the patient's aortic valve has opened in response to the reduction of speed.

In yet another embodiment, a ventricular assist device comprises a control circuit for controlling operation of the ventricular assist device in a patient, the control circuit comprises a memory for storing instructions and a processor for executing the instructions stored in the memory. The processor being is configured to obtain flow rate data from the ventricular assist device, the flow rate data indicating a rate of flow of blood exiting the ventricular assist device, and repeatedly determine whether the patient's aortic valve is one of open and closed based on the obtained flow rate data. If it is determined that the patient's aortic valve is closed based on one or more determinations, the operating speed of the ventricular assist device is reduced. The ventricular assist device further includes a housing and a rotary pump configured to be implantable in fluid communication with the patient's heart to assist blood flow from the heart, the rotary pump comprising an impeller disposed in the housing. A pump drive circuit in communication with the control circuit and the rotary pump is included, the pump drive circuit configured to supply power to the pump to drive the impeller and to control speed of the pump in response to control signals provided from the control circuit.

In another aspect of this embodiment, the control circuit determines whether the patient's aortic valve is one of open and closed when the rotary pump operates in a continuous flow mode.

In another aspect of this embodiment, the device further includes one or more sensors for sensing an amount of current used to drive the pump and a speed of the pump's rotor and providing data signals indicating the sensed amount of current and speed to the control circuit.

In another aspect of this embodiment, the control circuit determines a flow rate of blood exiting the pump based on the data signals from the one or more sensors.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 8 shows results of the above the method shown in FIG. 7 for a set of predictors and the accuracy, sensitivity, specificity, and balanced accuracy in predicting aortic valve opening or closing.

DETAILED DESCRIPTION

Figure 1:
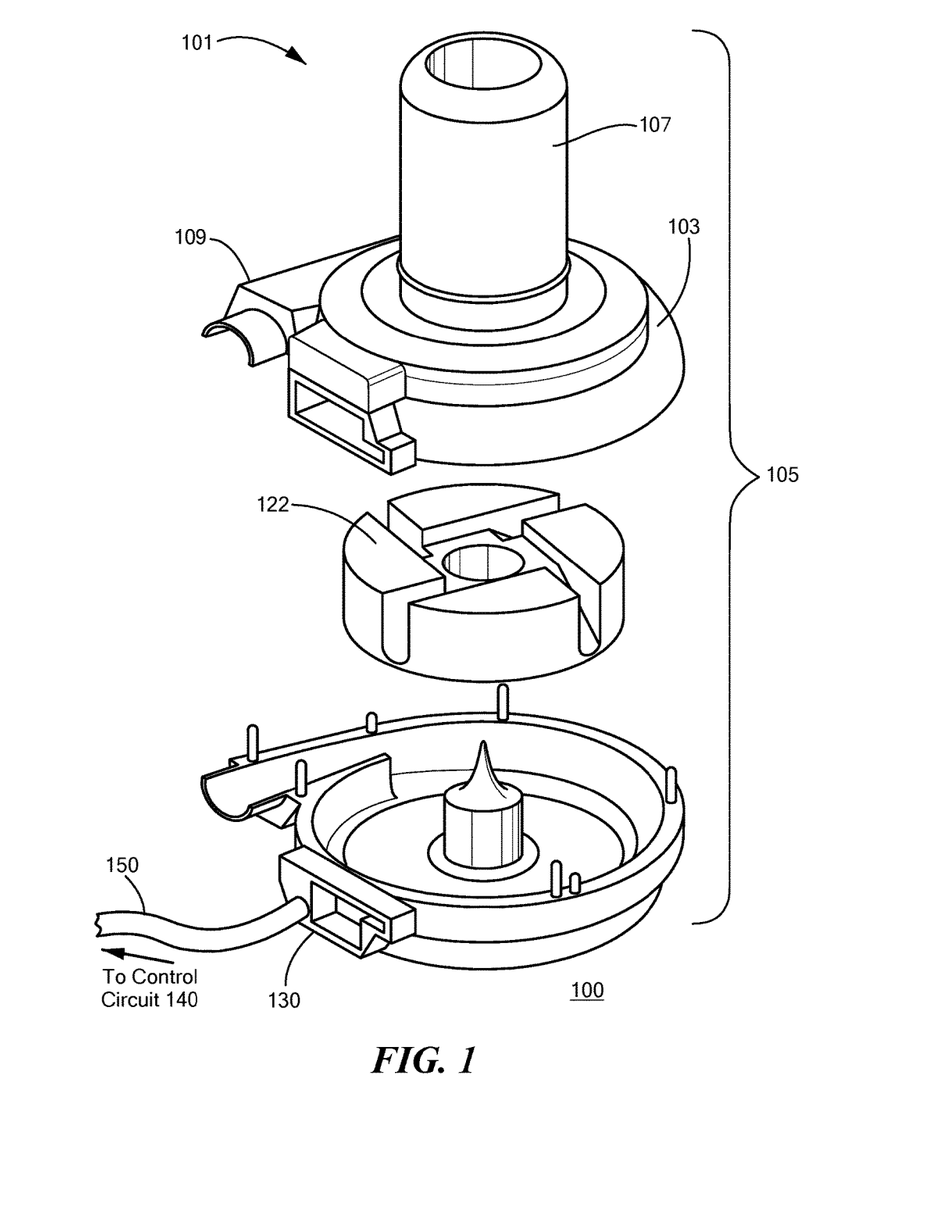
FIG. 1 is an exploded view an exemplary blood pump constructed in accordance with the principle of the present application.

Referring now to the drawings in which like reference designators refer to like elements, there is shown in FIG. 1 an exemplary blood pump constructed in accordance with the principle of the present application and designated generally as "101." The pump 101 includes a housing 105 including interlocking casings to form a closed pumping chamber 103 between them. Blood is supplied to the pump 101 through an axial inlet cannula 107 adapted for apical insertion into a heart ventricle. The cannula 107 is affixed to or may be integral with the housing 105 and is in fluid flow communication with the pumping chamber 103. Blood exits the pumping chamber 103 through an outlet in a direction substantially perpendicular to the longitudinal axis of the inlet cannula 107. The outlet of the housing can be connected to an artery of the patient, such as the aorta, by an outlet cannula 109.

A rotor or pump impeller 122 is located within the pumping chamber 103. The rotor incorporates one or more permanent magnets (not shown), and sets of electrical coils (not shown) are disposed in fixed locations within housing 105. The coils and magnets form a motor. In operation, blood entering the cannula 107 from a heart ventricle passes into the pumping chamber 103 where it is engaged by the rotating impeller 122. Blood entering the pumping chamber from the cannula 107 is redirected from axial flow exiting the cannula to a radial flow within which the impeller 122 is submerged.

A power and control cable 150 extends through a feedthrough 130 on the housing, and connects the coils within the housing to a control circuit 140. Control circuit 140 is connected to a source of electrical energy (not shown), which may include a storage battery, a mains power connection or both. As further discussed below, control circuit 140 is arranged to energize the coils of the pump in sequence so as to apply a rotating magnetic field within the housing and drive rotor 122 in rotation so that, in operation, the pump draws blood from the left ventricle V of the patient's heart and propels the blood through outflow cannula 109 into the patient's aorta.

The control circuit 140 monitors and further controls operation of the pump 101. The control circuit functions may be implemented at least in part by a general-purpose processor, as shown in the example implementation of FIG. 2. As shown, the control circuit 140 is implemented using a processor 210, a memory 220, data 230, instructions 240, and a pump interface 250. Interface 250 may include components such as power semiconductors connected to the coils of the pump, as well as one or more sensors for detecting voltages on the pump coils. The control circuit 140 may optionally include an I/O interface 252 which connects the control circuit 140 to one or more I/O devices 260 adapted to input information into the control circuit, output information from the control circuit, or both. The interface 250 may be an analog interface or a digital interface.

Figure 2:
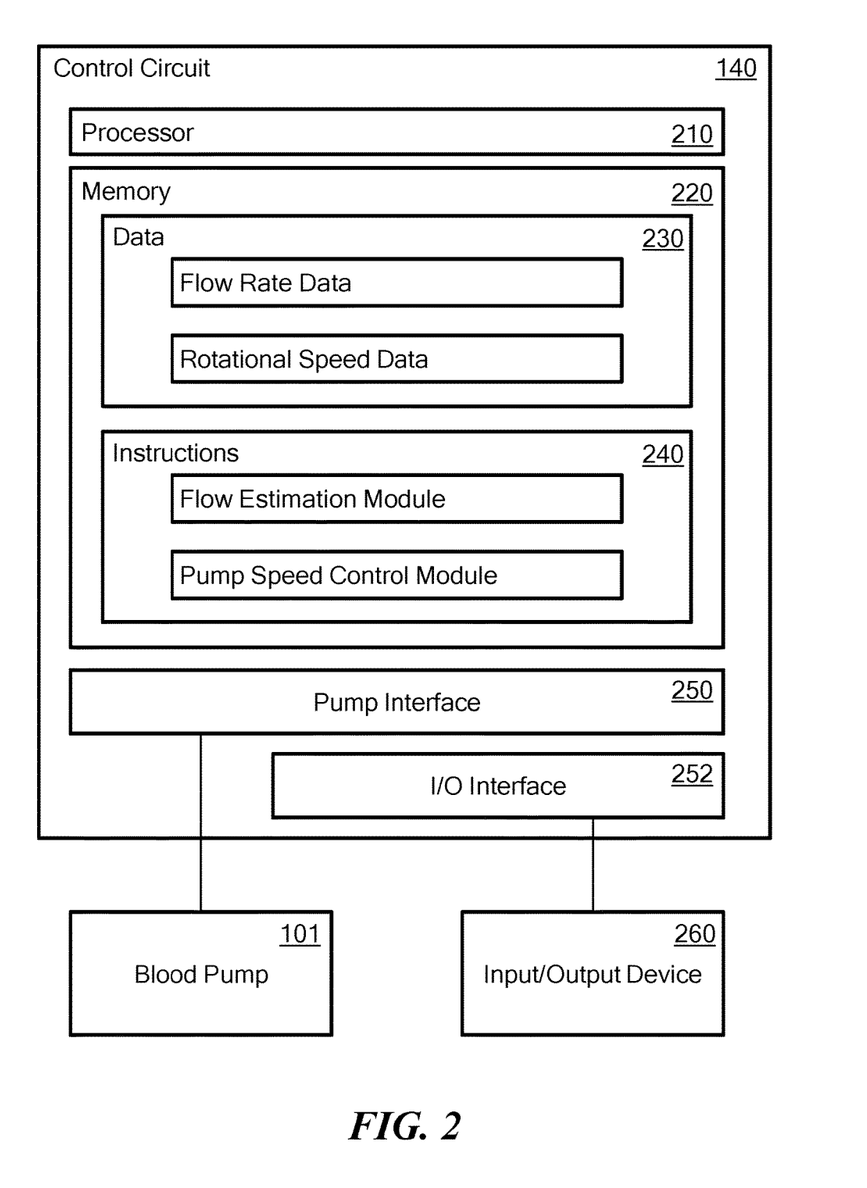
FIG. 2 shows a block diagram of the control circuit and blood pump of the present application.

Memory 220 stores information accessible by processor 210, including instructions 240 that may be executed by the processor 210. The memory also includes data 230 that may be retrieved, manipulated or stored by the processor 210. The memory may be of any type capable of storing information accessible by the processor, such as a hard-drive, memory card, ROM, RAM, DVD, CD-ROM, write-capable, and read-only memories. The processor 210 may be any well-known processor, such as commercially available processors. Alternatively, the processor may be a dedicated controller such as an ASIC.

Data 230 may be retrieved, stored or modified by processor 210 in accordance with the instructions 240. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data. The instructions stored in the memory may include one or more instruction sets or modules for performing certain operations. One such module may be a flow estimation module for performing the steps required to estimate a flow rate of blood through the pump. Another such module may be a pump control module for controlling the speed of the pump speed control module. Another such module may be a suction detection module for determining the presence of a suction condition and taking actions in response to the same.

Although FIG. 2 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

Additionally, the control circuitry of the present disclosure may be configured to store data (e.g., flow rate data, rotational speed data, flow derivatives, aortic valve open/closed determinations, etc.) and instructions (e.g., flow estimation, pump speed control, cardiac cycle identification, systole identification, inflection point identification, index determination (as discussed below), aortic valve open/closed determination, etc.) in accordance with the disclosure herein.

The blood pump may provide only partial support to the patient. In such cases, the patient's heart continues to pump blood from the left ventricle to the aorta through the aortic valve (or, in the case of the right ventricle, to the pulmonary artery through the pulmonic valve), and the blood pump further assists the activity of the patient's heart in parallel. Although the heart only pumps blood into the aorta during systole, the blood pump, which typically bypasses the aortic valve and propels blood directly into the vasculature (e.g. aortic artery), works during both systole and diastole, when the aortic valve is open or closed. The data of the examples provided herein generally show a blood pump operating in a continuous flow mode, but in other instances, the blood pump may operate in a pulsatile flow mode. In either case, over a given period of time including systole and diastole, the patient's heart and the blood pump may each be responsible for some of the work performed to pump blood to the patient's arteries.

It is generally understood that increasing the speed of the blood pump causes the pump to perform more work. In some cases, increasing the speed of the pump may be beneficial for the patient, by allowing the pump to perform additional work in tandem with the heart. However, in other cases, the pump may already be operating at a speed at which there is little or no additional work to be performed (e.g., blood to be pumped from the ventricle), in which case increasing the pump speed may simply cause the patient's heart to perform less work, but not necessarily increase the overall work performed. In some cases, increasing motor speed of the blood pump may leave so little work for the heart that the aortic valve is not forced open during systole, thereby transitioning the pump from a state of partial-assistance to a state of full-assistance. Such transitions from a state of partial-assistance to a state of full-assistance, leaving the aortic valve closed for long durations of time, may be unwanted. Therefore, it is desirable to determine whether the aortic valve of a patient is open or closed during systole of the patient's cardiac cycle. The ability of the aortic valve to open and close during a cardiac cycle relates to the degree that the patient's native heart maintains its physiological functions.

The present disclosure provides for methods and devices for determining whether the aortic valve of a patient is open or closed during systole of the patient's cardiac cycle (the "aortic valve determination"). More specifically, the present disclosure provides for such an aortic valve determination to be made using data indicative of a flow rate of blood exiting a blood pump in communication with the patient's heart. The data may be collected and processed by a control circuit of the blood pump in order to derive the aortic valve determination. In this regard, it is possible for the control circuit to make the aortic valve determination even with limited processing capability (e.g., linear and exponent operations).

The present disclosure further provides for methods and devices for controlling operation of a blood pump based on the aortic valve determination. More specifically, the present disclosure provides for control of the blood pump based on repeated aortic valve determinations. In this regard, even if any given aortic valve determination is subject to error, such error can be mitigated using several consistent (or mostly consistent) aortic valve determinations.

Figure 3A:
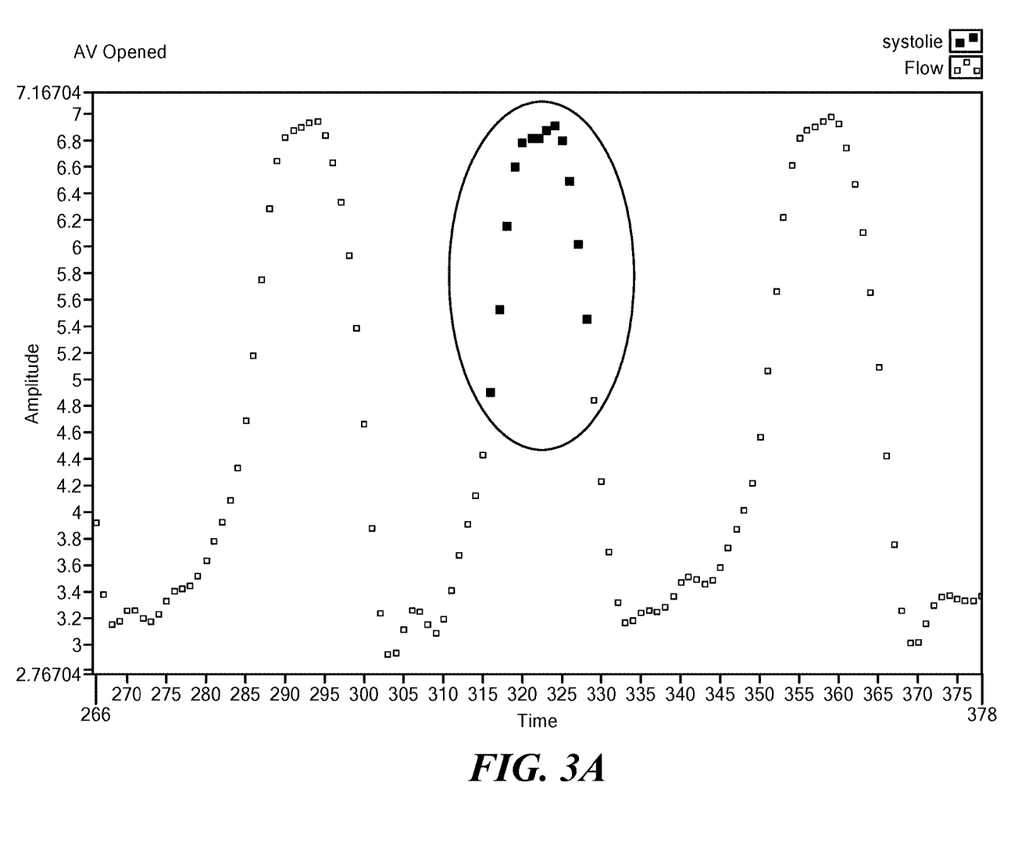
FIG. 3A is a graph showing flow in the exemplary blood pump shown in FIG. 1 with the aortic valve open and systolic portions highlighted.
Figure 3B:
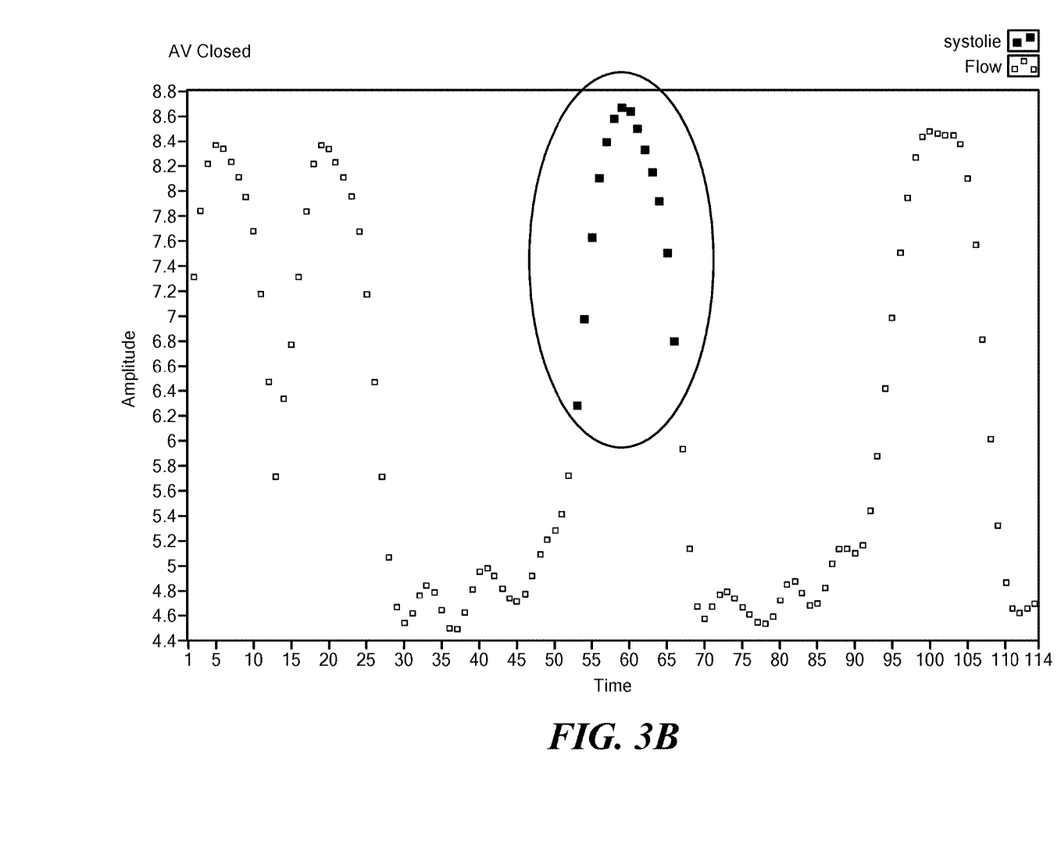
FIG. 3B is a graph showing flow in the exemplary blood pump shown in FIG. 1 with the aortic valve closed and systolic portions highlighted.

FIG. 3A shows an example waveform of flow rate data collected from a patient during a duration of cardiac activity for which the aortic valve is open. By comparison, FIG. 3B shows an example waveform of flow rate data for which the aortic valve is closed. As can be seen from FIGS. 3A and 3B, each waveform comprises a plurality of discrete data points, corresponding to flow rate measurements made at discrete points in time. The flow rate measurements may be measured estimated, calculated, or otherwise determined using data received by the control circuit. Commonly owned U.S. Pat. No. 8,897,873 and Publication Nos. 2012/0245681, 2015/0367048, 2016/0166211 provide some examples of methods, control circuits and systems for flow rate data collection, and the disclosures of those applications are hereby incorporated by reference herein in their entireties.

In each of FIGS. 3A and 3B, the peak of the systolic portion of the waveform is circled. As can be seen from the figures, the peak is smoother and less skewed when the aortic valve is closed than when the aortic valve is open. Although the shape of each peak may be different from one peak to the next, peaks associated with a closed aortic valve generally exhibit more smoothness and less skew than peaks associated with an open aortic valve. Thus, the peaks may be classified as "open" or "closed" depending on their properties. Properties of the peaks, such as skew and smoothness, may be characterized mathematically.

Figure 4:
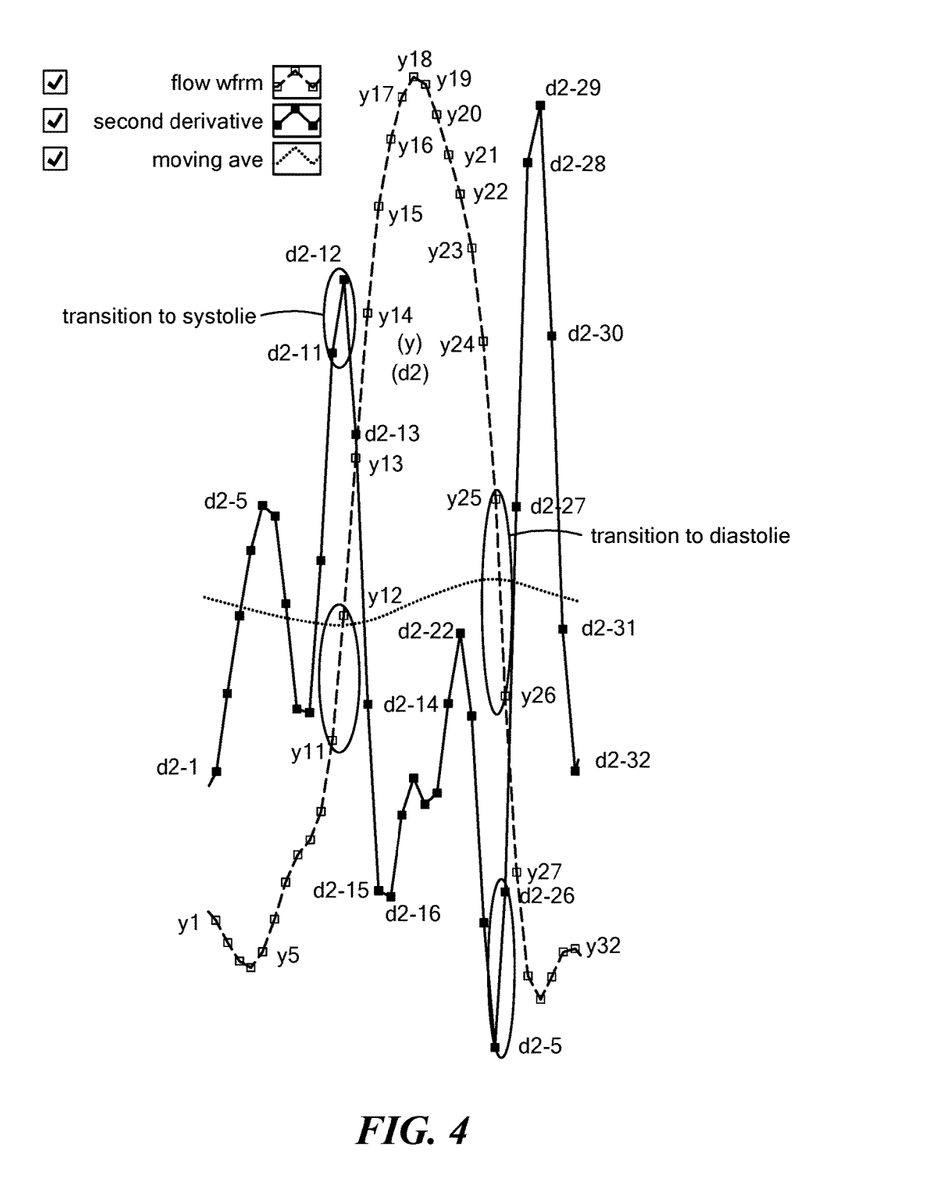
FIG. 4 is a graph showing a waveform formed by discrete flow rate measurement data points over time.

In order to characterize the properties of the peaks, which at least a part of the systolic portion of the flow rate waveform, the peaks must first be identified. At least part of the systolic portion of the waveform may be identified based on inflection points in the waveform. For example, FIG. 4 shows a waveform formed by discrete flow rate measurement data points (y) over time. Given that there is an equal amount of time between each flow rate measurement, a first derivative of each data point may be determined by calculating a difference between that data point and the previous data point. The inflection point may then be identified as the first derivative having the greatest absolute value (local extremum of the first derivatives, or, for the second derivatives of the data points, a zero-crossing of the second derivatives). In the example of FIG. 4, the inflection point is also characterized by way of a plot of the second derivative (d2) of the flow rate waveform. In the case of a transition to systole, meaning the beginning of systole, the point of inflection is characterized by a maximum in the second derivative (y12, corresponding to maximum d2-12). Conversely, in the case of a transition to diastole, meaning the end of systole, the point of inflection is characterized by a minimum in the second derivative (y25, corresponding to minimum d2-25).

In other instances, at least part of the systolic portion of the waveform may be identified based in part on a filtered version of the waveform, such as a running average or weighted average using several previous waveform data points. For example, FIG. 4 also shows a filtered waveform, particularly a moving average (solid line, no data points), superimposed over the flow rate waveform. A transition to systole may then be indicated by the flow rate data point (e.g., y12) that exceeds the filtered waveform. Likewise, a transition to diastole may be indicated by the flow rate data point (e.g., y26) that drops below the filtered waveform, meaning that the previous data point (y25) is the last data point of the systolic portion of the flow rate waveform.

In further instances, the filtered waveform may also be accompanied by threshold markers (dotted lines) positioned above and below the filtered waveform (e.g., a set amount above or below, a percentage above or below, etc.). Transition to systole or diastole may be indicated by the first flow rate measurement crossing the filtered waveform or one of the markers (e.g., nearing or exceeding the filtered waveform, also referred to as a "crossover point").

The particular part of the systolic portion of the waveform that is desired to be identified may vary depending on the property that is being evaluated. For example, if skew of the peak is being evaluated, then it may be desirable to identify the entire systolic portion. For further example, if smoothness of the peak is being evaluated, it may be desirable to identify only the part of the systolic portion for which the first derivative of the flow rate curve is decreasing.

Figure 5:
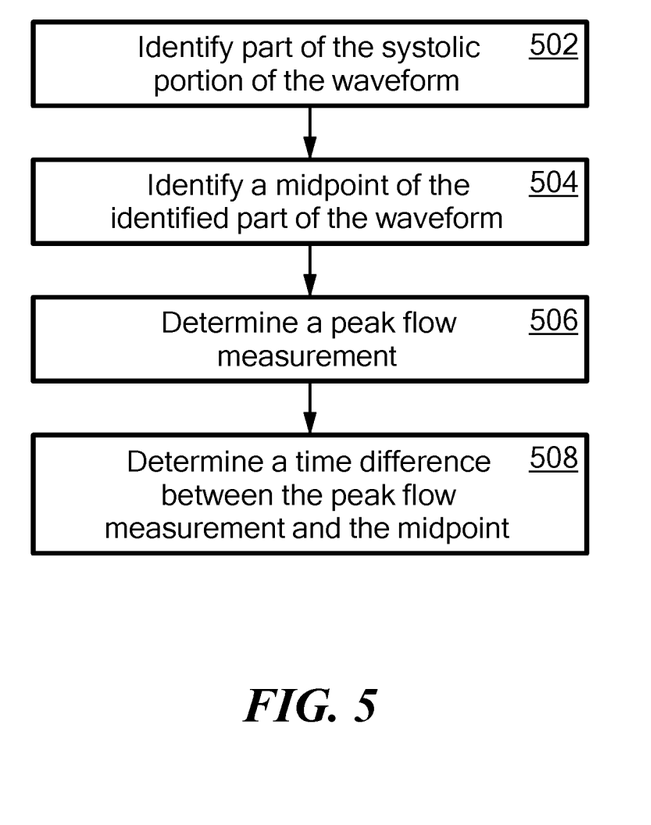
FIG. 5 is a flow chart showing a method of determining a time different between a peak flow measurement and a midpoint of flow measurement.

FIG. 5 provides an example method of characterizing the skew of the peak. At 502, at least a part of the systolic portion of the waveform is identified. At 504, a midpoint of the identified part of the waveform is identified. The midpoint may be identified by first determining a total number N of flow rate data points associated with the systolic portion of the waveform, and then identifying the middle data point $Q_{N/2}$.

At 506, a peak flow rate measurement $Q_{peak}$ is determined. At 508, a time difference between the midpoint and the peak flow, $t(Q_{N/2})-t(Q_{peak})$, is determined. The magnitude of the time difference may indicate how far the peak flow rate occurs from the midpoint of systole. Whether the difference is positive or negative may also indicate whether the peak flow rate occurs before or after the midpoint of systole. This information is effectively a characterization of the skew of the systolic portion of the flow rate waveform.

Figure 6A:
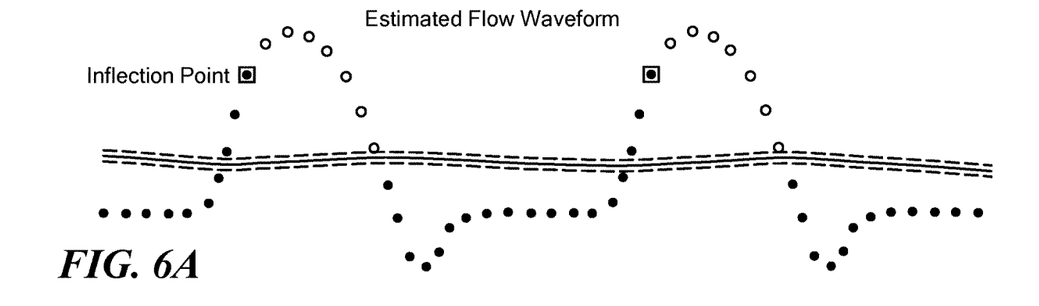
FIG. 6A shows an estimated flow waveform in which the data points beginning with the inflection point at the beginning of systole (boxed) and ending with the data point preceding the measurement below the filtered waveform are evaluated.
Figure 6B:
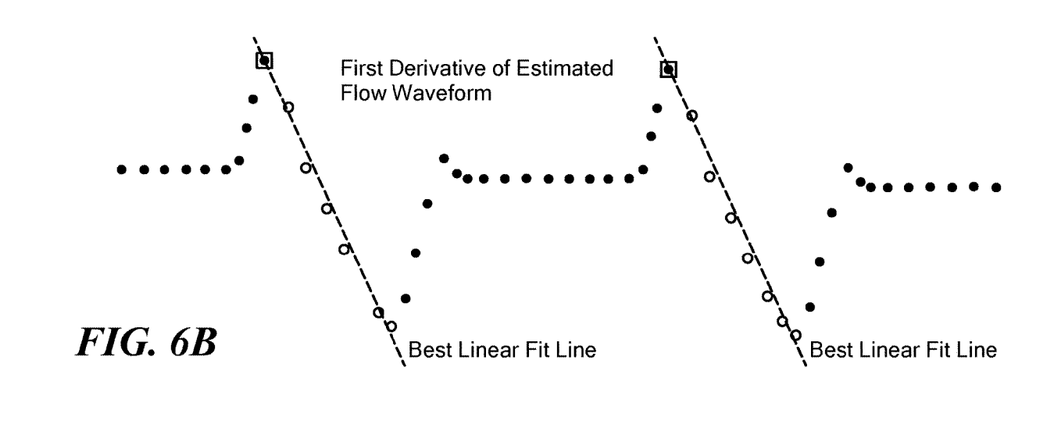
FIG. 6B shows the first derivative of the evaluated data points shown in FIG. 6A, as well as a best linear fit line superimposed on the first derivative.
Figure 7:
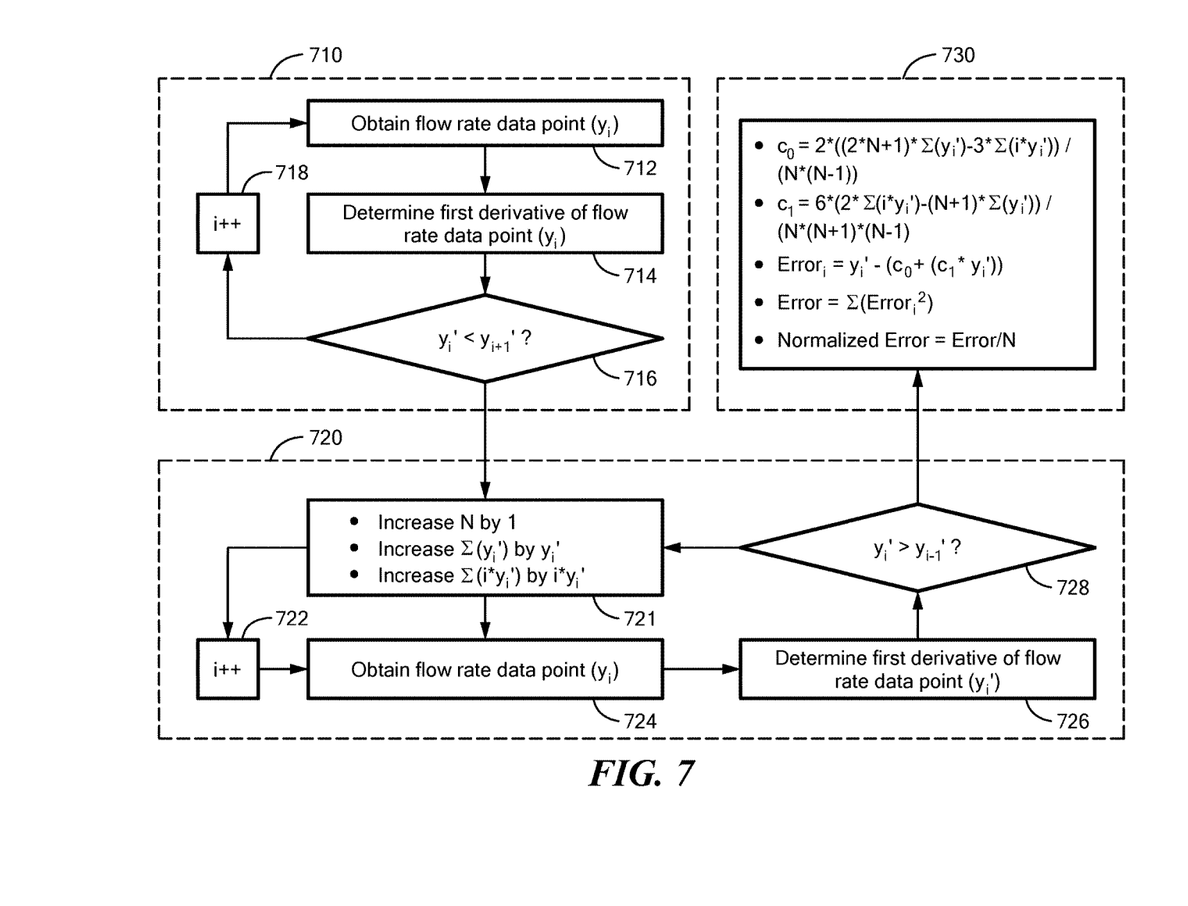
FIG. 7 is a flow chart illustrating the method of determining the flow data points shown in FIGS. 6A and 6B.

FIGS. 6A, 6B and 7 show an example of smoothness being characterized based on a normalized linear mean square error of the first derivative of the measured flow rate data points. FIG. 6A shows an estimated flow waveform in which the data points beginning with the inflection point at the beginning of systole (boxed) and ending with the data point preceding the measurement below the filtered waveform are evaluated. FIG. 6B shows the first derivative of the evaluated data points, as well as a best linear fit line superimposed on the first derivative.

The mean linear square error of the first derivative of the data points may then be calculated using:

$$\text{Mean Square Error} = \frac{1}{N}\sum_{i=1}^{N}(c_1 x_i + c_0 - y'_i)^2 \qquad (1)$$

where $y'_i$ is the derivative of the estimated flow rate for each of the N evaluated data points, $x_i$ is the time each respective data point is obtained (e.g., first flow rate data point $y_1$ at time $x_1=1$, second flow rate data point $y_2$ at time $x_2=2$, etc.), and $c_0$ and $c_1$ are coefficients of the mean square error equation. The mean square error (MSE) is minimized by finding the coefficients $c_0$ and $c_1$ that satisfy:

$$\frac{\partial MSE(c_1, c_0)}{\partial c_1} = \frac{\partial MSE(c_1, c_0)}{\partial c_0} = 0 \qquad (2)$$

This results in two sets of equations:

$$c_0 \sum_{k=0}^{N} x_k^0 + c_1 \sum_{k=0}^{N} x_k^1 = \sum_{k=0}^{N} y_i' \qquad (3)$$

$$c_0 \sum_{k=0}^{N} x_k^1 + c_1 \sum_{k=0}^{N} x_k^2 = \sum_{k=0}^{N} x_i y_i' \qquad (4)$$

These sums can be further simplified as:

$$\sum_{k=0}^{N} x_k^0 = N \qquad (5)$$

$$\sum_{k=0}^{N} x_k^1 = \frac{N(N+1)}{2} \qquad (6)$$

$$\sum_{k=0}^{N} x_k^2 = \frac{N(N+1)(2N+1)}{6} \qquad (7)$$

This means that coefficients $c_0$ and $c_1$ may be calculated using the following equations:

$$c_0 = \frac{2\left[(2N+1)\sum_{k=0}^{N} y_i' - 3\sum_{k=0}^{N} i \cdot y_i'\right]}{N(N-1)} \qquad (8)$$

$$c_1 = \frac{6\left[2\sum_{k=0}^{N} y_i' - (N+1)\sum_{k=0}^{N} i \cdot y'^i\right]}{N(N-1)(N+1)} \qquad (9)$$

A control circuit may be capable of calculating $c_0$ and $c_1$ using the above equations without having to perform any operations other than arithmetic. Additionally, the control circuit may use as few as three counters or accumulators to keep track of N, $\Sigma(y'_i)$ and $\Sigma(i*y'_i)$ as the flow rate data points are obtained. Once all the flow rate data points for evaluation are obtained and the accumulators are summed to their respective final results, $c_0$ and $c_1$ may be calculated using the equations above.

FIG. 7 provides a method for performing the operations described above. At 710, a beginning of a systolic peak portion of the flow rate data (e.g., a point of inflection) is identified. Identifying the systolic peak portion of the waveform may be accomplished, in the course of obtaining flow rate data points, by obtaining a flow rate data point $y_i$ (712) at time $x_i$, determining the first derivative of the flow rate data point $y'_i$ (for example, using the following equation: $(y_i - y_{i-1})/(x_i - x_{i-1})$) (714), and comparing the first derivative of the flow rate data point $y'_i$ to the first derivative of the previous flow rate data point $y'_{i-1}$ (716). If $y'_i$ is greater than or equal to $y'_{i-1}$, then operations continue with obtaining the next flow rate data point $y_{i+1}$, or otherwise termed $y_i$ (712) after i is increased by 1 (718).

If $y'_i$ is less than $y'_{i-1}$, then operations continue at 720 with collecting data for determining normalized error. The data is collected until an end of the systolic peak portion of the flow rate data (e.g., a next point of inflection) is identified. For each data point in the systolic peak portion of the flow rate data, a first accumulator ("N" or "i") is summed by one, a second accumulator is summed by the first derivative of the data point, and the third accumulator is summed by the product of the first and second accumulators (721). Operations continue with obtaining the next flow rate data point $y_{i+1}$, or otherwise termed $y_i$ (724) after i is increased by 1 (722). Then, the first derivative of the next flow rate data point $y'_i$ is determined (726). Then $y'_i$ is compared to the first derivative of the previous flow rate data point $y'_{i-1}$ (728). If $y'_i$ is less than $y'_{i-1}$, then $y_i$ is still part of the systolic peak portion and operations continue with collecting data for $y_i$ (721).

If $y'_i$ is greater than or equal to $y'_{i-1}$, then $y_i$ is not part of the systolic peak portion. With the flow rate data points for the entire systolic peak portion having been collected, operations continue at 730 with calculating the normalized error. The equations for calculating a normalized mean linear square error are presented above, and involve first calculating coefficients $c_0$ and $c_1$ based on the values in the three accumulators, then plugging those coefficients into the equation for mean linear square error (which is the sum of squared error for each individual data point $Error_i$), and then normalizing the error by dividing by the total number of evaluated data points.

More generally, other properties of the flow rate waveform may also be characterized, and skew and smoothness are just two of many properties of the flow rate waveform. In this regard, the skew characterization above may be thought of a first index, and the normalization characterization above may be thought of as a second index. Other indices, characterizing other properties, that may be determined include, but are not limited to, the following:

raw_Intg: The integral (area under the curve) of the evaluated part of the systolic portion of the flow rate waveform.

tpoints: The number of data points in the evaluated part of the systolic portion of the flow rate waveform.

SdiffY: the difference in flow rate between adjacent data points, summed for all data points over the evaluated part of the systolic portion of the flow rate waveform.

SsqrDiffY: the square of the difference in flow rate between adjacent data points, summed for all data points over the evaluated part of the systolic portion of the flow rate waveform.

S(Y-Ym)^3: the cube of the difference between the max flow rate and a given flow rate data point, summed for all data points over the evaluated part of the systolic portion of the flow rate waveform.

Indices may also include running averages of any of the above features, such as a running average of any of the above properties over the previous 5 or 10 cardiac cycles.

The aortic valve determination of the present disclosure may be made based at least in part on two or more determined indices. For example, the indices may be combined using the following linear combination:

$$\text{Combined Index} = A_0 + A_1 I_1 + A_2 I_2 \qquad (10)$$

In which $I_1$ is a first index (e.g., skew), $I_2$ is a second index (e.g., normalization), and $A_0$, $A_1$ and $A_2$ are constant values. $A_0$, $A_1$ and $A_2$ may be predetermined based on a linear discriminant analysis performed earlier in time, scaling factors (e.g., due to differences in scale between the various computed indices), or any combination thereof.

Optionally, the Combined Index itself may be scaled in order to more distribute the index results in a manner that more readily indicates the index results to an observer. For instance, the Combine Index may be scaled to result in a numerical output between 1 and 7, in which 1 indicates a strong likelihood of aortic valve closing, 7 indicates a string likelihood of aortic valve opening, and number in between indicate aortic valve closing (2-3) or opening (4-5) and varying degrees of likelihood.

Figure 9:
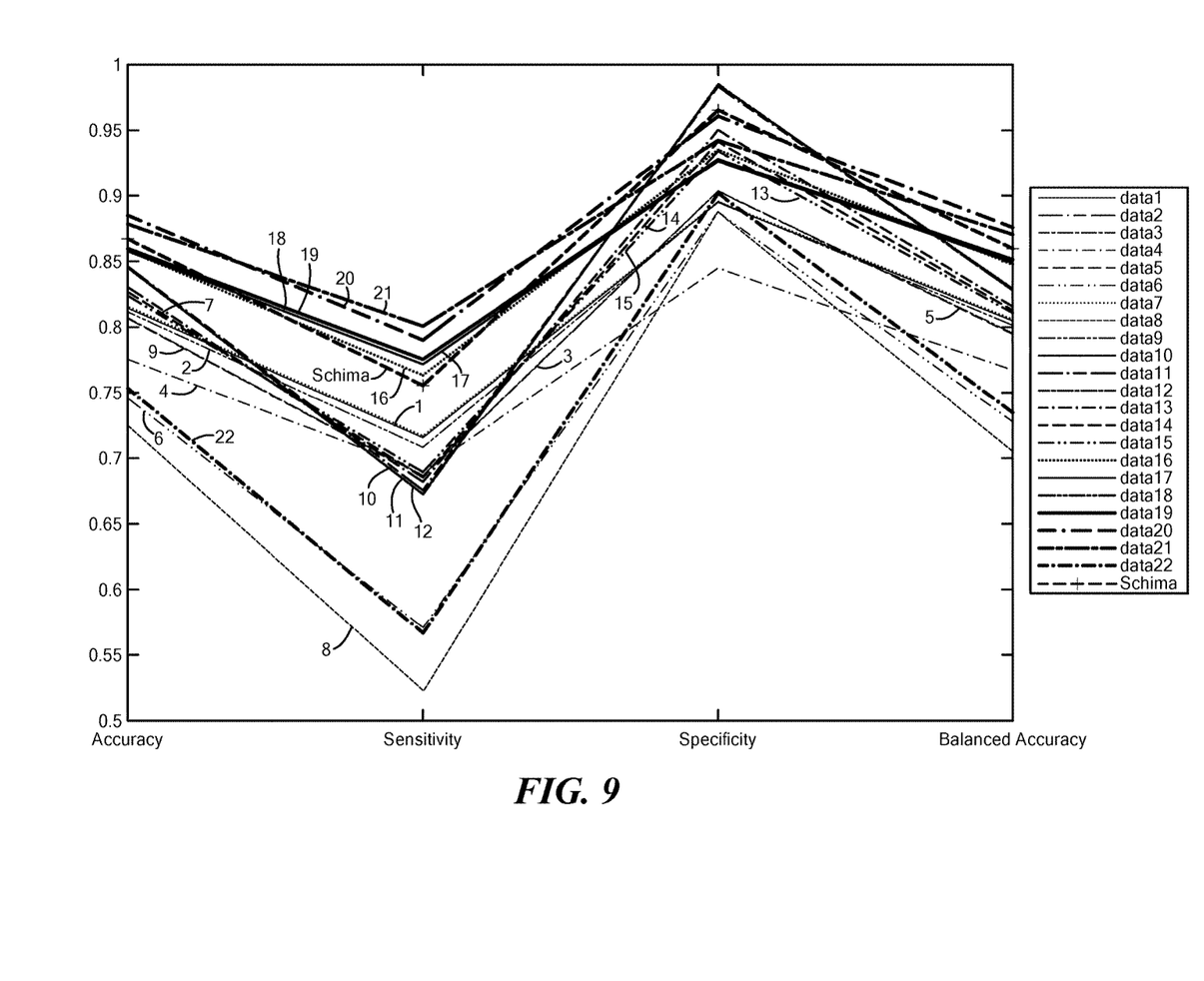
FIG. 9 shows a graphical result of the results shown in FIG. 8.

FIGS. 8 and 9 show test results for a list of sets of various features (also referred to as indices, or as predictors) that were evaluated as potential predictors in linear discriminant analysis. The results shown in FIGS. 8 and 9 were derived from a combination of flow rate measurements from the ventricular assist devices of 15 patients. Specifically, FIGS. 8 and 9 shows for each tested set of predictors (listed in FIG. 8), the accuracy, sensitivity, specificity, and balanced accuracy in predicting aortic valve opening or closing. Notably, Set #20 of FIG. 8 takes the running average of norm_Er (normalized error, or smoothness) and Dt (skew) over 5 cardiac cycles, and provides an aortic valve determination with about 86% accuracy, about 78% sensitivity, about 93% specificity, and about 85% balanced accuracy. Even more notably, only arithmetic and exponentiation operators are needed in order to make an aortic valve determination using the indices of Set #20.

In some instances, an aortic valve determination may be associated with a strong degree of likelihood (e.g., 1 or 7), indicating with near certainty that the aortic valve is open or closed. However, in other instances in which the aortic valve determination is not associated with the same degree of certainty, the certainty of aortic valve opening or closing may be enhanced by combining several aortic valve determinations together. In other words, if the control circuit determines that the aortic valve is closed with 75% certainty, then there is only a 75% likelihood that the aortic valve is in fact closed. But if the control circuit determines a few consecutive times that the aortic valve is closed with 75% certainty, then the likelihood of the aortic valve being closed may rise (e.g., above 80%, above 90%, even above 99%).

In some examples, the overall degree of certainty $P_{overall}$ derived from N aortic valve determinations may be estimated using the following equation:

$$P_{overall} = (1 - P_1) * (1 - P_2) * \ldots * (1 - P_N) \quad (11)$$

In such examples, the overall degree of certainty could then be compared to a threshold (e.g., 90%) to determine certainty that the aortic valve is open or closed. Alternatively, the degree of certainty could be based on a predefined consecutive number of determinations exceeding a threshold certainty value (e.g., 8 consecutive determinations exceeding 70% certainty, 4 consecutive determinations exceeding 85% certainty, 3 consecutive determinations exceeding 99% certainty, etc., including any combination of the above).

The control circuit may further control operation of the VAD in response to the aortic valve determination. For instance, if it is determined that the aortic valve has remained closed during systole for a certain threshold amount of time, the control circuit may reduce the speed of the VAD, thereby reducing the amount of work performed by the VAD and leaving more work to be performed by the patient's heart. This in turn may result in the aortic valve opening due to a stronger contraction at the left ventricle of the patient's heart. Speed reduction may be performed in intervals of 200 RPM until the VAD pump speed reaches a predetermined lower speed (e.g., 1800 RPM), or until it is determined with a sufficient degree of certainty that the aortic valve is open during systole. The threshold amount of time, the degree of certainty for aortic valve opening, and the degree of certainty for aortic valve closure, may all be preset values stored in a memory of the control circuit.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A method for determining whether a patient's aortic valve is open or closed, comprising:
    obtaining a plurality of flow rate data points from a blood pump implanted within the patient, each flow rate data point indicating a then-current flow rate of blood exiting the pump;
    identifying a portion of the flow rate data points associated with systole of a given cardiac cycle of the patient by;
        determining a running average of flow rate;
        comparing the obtained flow rate data points to the running average, a flow rate data point crossing above a crossover value of the running average being indicative of a beginning of systole, and a flow rate data point crossing below a crossover value of running average being indicative of an end of systole; and
        identifying the portion of flow rate data points above the running average as being associated with systole;
    determining a first index value characterizing a first property of at least part of the identified portion of the flow rate data points;
    determining a second index value characterizing a second property of at least part of the identified portion of the flow rate data points;
    determining whether the patient's aortic valve is one of open and closed based on the first and second index values; and
    adjusting a speed of an impeller of the blood pump when the aortic valve is determined to be closed.

2. The method of claim 1, further comprising determining a first derivative for each of the obtained plurality of flow rate data points, wherein at least one of the first and second index values is determined based on the determined first derivatives.

3. The method of claim 2, wherein the first derivative for each given flow rate data point is determined by the difference between the given flow rate data point and the preceding flow rate data point.

4. The method of claim 1, wherein identifying a portion of the flow rate data points associated with systole comprises:
    determining a first derivative of each of the flow rate data points; and
    identifying the portion of flow rate data points for which the first derivative decreases as associated with systole.

5. The method of claim 1, wherein the first index value characterizes skew of the identified portion of the flow rate data points, and wherein the second index value characterizes smoothness of the identified portion of the flow rate data points.

6. The method of claim 5, wherein the first index value characterizing skew is determined based on the difference in time between the flow rate data point indicating maximum flow rate and the midpoint of the identified portion of the flow rate data points.

7. The method of claim 5, wherein the second index value characterizing smoothness is determined based on a mean linear square error between the first derivatives of the flow rate data points and a best fit line.

8. The method of claim 7, wherein the mean linear square error is determined based at least in part on (i) a total number of evaluated flow rate data points, (ii) a sum of the first derivatives of the evaluated flow rate data points, and (iii) a product of (i) and (ii).

9. The method of claim 5, wherein determining whether the patient's aortic valve is one of open and closed is based on a running average of the first and second index values for five previous cardiac cycles.

10. The method of claim 1, wherein determining whether the patient's aortic valve is one of open and closed is based on a scaled linear combination of the first and second index values.

11. The method of claim 10, wherein the scaled linear combination is based on a plurality of coefficients previously determined during a linear discriminant analysis using the first and second indices.

12. A ventricular assist device, comprising:
a control circuit for controlling operation of the ventricular assist device implanted within a patient, the control circuit comprising:
  a memory for storing instructions; and
  a processor for executing the instructions stored in the memory, the processor being configured to:
    obtain a plurality of flow rate data points from the ventricular assist device, each flow rate data point indicating a then-current flow rate of blood exiting the ventricular assist device;
    identify a portion of the flow rate data points associated with systole of a given cardiac cycle of the patient by;
      determining a running average of flow rate;
      comparing the obtained flow rate data points to the running average, a flow rate data point crossing above a crossover value of the running average being indicative of a beginning of systole, and a flow rate data point crossing below a crossover value of running average being indicative of an end of systole; and
      identifying the portion of flow rate data points above the running average as being associated with systole;
    determine a first index value characterizing a first property of at least part of the identified portion of the flow rate data points;
    determine a second index value characterizing a second property of at least part of the identified portion of the flow rate data points;
    determine whether the patient's aortic valve is one of open and closed based on the first and second index values; and
an impeller disposed in a housing of the ventricular assist device in fluid communication with the patient's heart; and
a pump drive circuit in communication with the control circuit and the ventricular assist device, the pump drive circuit configured to supply power to the ventricular assist device to drive the impeller and to control speed of the impeller in response to control signals provided from the control circuit.

13. The device of claim 12, wherein the control circuit determines whether the patient's aortic valve is one of open and closed when the ventricular assist device operates in a continuous flow mode.

14. The device of claim 12, further comprising one or more sensors for sensing an amount of current used to drive the ventricular assist device and a speed of the impeller and providing data signals indicating the sensed amount of current and speed to the control circuit.

15. The device of claim 14, wherein the control circuit determines a flow rate of blood exiting the ventricular assist device based on the data signals from the one or more sensors.

* * * * *